United States Patent [19]

Sun

[11] Patent Number: 4,846,189

[45] Date of Patent: Jul. 11, 1989

[54] NONCONTACTIVE ARTERIAL BLOOD PRESSURE MONITOR AND MEASURING METHOD

[76] Inventor: Shuxing Sun, Shanghai Institute of Biomedical Engineering, Shanghai University of Science and Technology, Shanghai, China

[21] Appl. No.: 68,107
[22] Filed: Jun. 29, 1987
[51] Int. Cl.$^4$ .................................... A61B 5/02
[52] U.S. Cl. ............................ 128/679; 128/667
[58] Field of Search .................... 128/679–683, 128/666–667, 687–690

[56] References Cited

U.S. PATENT DOCUMENTS

| | | | |
|---|---|---|---|
| 3,229,685 | 1/1966 | Ringkam et al. | 128/2.05 |
| 3,412,729 | 11/1968 | Smith, Jr. | 128/667 X |
| 3,704,706 | 12/1972 | Herczfeld et al. | 128/2 R |
| 3,769,974 | 11/1973 | Smart et al. | 128/2.05 P |
| 3,993,047 | 11/1976 | Peek | 128/2.05 P |
| 3,998,550 | 12/1976 | Konishi et al. | 356/39 |
| 4,167,331 | 9/1979 | Nielsen | 356/39 |
| 4,266,554 | 5/1981 | Hamaguri | 128/633 |
| 4,280,505 | 7/1981 | Dali et al. | 128/635 |
| 4,290,431 | 9/1981 | Herbert et al. | 204/195 P |
| 4,301,807 | 11/1981 | Mentelos | 128/635 |
| 4,407,920 | 10/1983 | Wilber | 128/633 |
| 4,437,470 | 3/1984 | Prost | 128/679 |
| 4,446,871 | 5/1984 | Imura | 128/633 |
| 4,524,777 | 6/1985 | Kisioka et al. | 128/677 |
| 4,541,901 | 9/1985 | Parker et al. | 204/1 T |
| 4,566,563 | 1/1986 | Taniguchi et al. | 128/682 |
| 4,581,714 | 4/1986 | Reid | 364/571 |
| 4,586,149 | 4/1986 | Stillman et al. | 364/557 |
| 4,586,513 | 5/1986 | Hamaguri | 128/633 |
| 4,601,293 | 7/1986 | Foster et al. | 128/635 |
| 4,603,700 | 8/1986 | Nichols et al. | 128/633 |
| 4,621,643 | 11/1986 | New, Jr. et al. | 128/633 |

FOREIGN PATENT DOCUMENTS 1538695  1/1979  United Kingdom ............... 128/667

OTHER PUBLICATIONS

K. Yamakashi et al., "Noninvasive Automatic Monitoring of Instantaneous Arterial Blood Pressure Using the Vascular Unloading Technique", *Medical & Biological Engineering & Computing,* pp. 557–565, (Sep. 1983).
K. Yamakoshi et al., "New Oscillometric Method for Indirect Measurement of Systolic and Mean Arterial Pressure in the Human Finger, Part I: Model Experiment.; Part II: Correlation Study" *Medical & Biological Engineering & Computing,* pp. 307–318, (May 1982.).
H. H. Hardy et al., "On the Pressure–Volume Relationship in Circulatory Elements", *Medical & Biological Engineering & Computing,* pp. 565–570, (Sep. 1982).
Paul D. Stein et al., "Arterial Tonometry for the Atraumatic Measurement of Arterial Blood Pressure", *Journal of Applied Physiology,* vol. 30, No. 4, pp. 593–596, (Apr. 1971).
K. Yamakoshi et al., "Indirect Measurement of Instantaneous Arterial Blood Pressure in the Human Finger by the Vascular Unloading Technique", *IEEE Transactions on Biomedical Engineering,* vol. BME-27, No. 3, (Mar. 1980).
Advertisement entitled, "With the Finapres Continuous NIBP Monitor, the Pressure is Always On", BOC Heath Care, (1986).
Advertisement entitled, "Ambulatory Blood Monitoring System, Model BP-100", M. E. Commerical Corp., (Date unknown).
Advertisement entitled, "The Nellcor N-100 Pulse Oximeter, Setting the Standard in Hypoxemia Monitoring", Nellcor, (1985).
Advertisement entitled, "Critikon Breaks the Time Barrier", Critikon, Inc., (1985).

*Primary Examiner*—Francis Jaworski
*Attorney, Agent, or Firm*—Workman, Nydegger & Jensen

[57] ABSTRACT

An automatic, continuous, non-occlusive blood pressure monitor includes a pressure applying cuff for temporarily applying pressure to a person's finger, a light source for illuminating the finger and an artery in the finger, a photosensor for detecting light transmitted through or reflected from the finger and for producing a signal representing relative volume of a unit length of the artery, a pressure sensor for producing a pressure signal representing the pressure applied by the cuff to the finger, and a microprocessor for developing from the relative volume signal and the pressure signal a formulation of arterial pressure P(t) as a function of relative arterial volume, and for calculating the arterial pressure P(t) from the relative volume signals.

7 Claims, 4 Drawing Sheets

NONCONTACTIVE ARTERIAL BLOOD PRESSURE MONITOR AND MEASURING METHOD

BACKGROUND OF THE INVENTION (a) Field of the Invention

This invention relates to arterial blood pressure monitoring and more particularly to a method and apparatus for continuous and nonn-contactive blood pressure measurement.

(b) Description of the Prior Art

Continuous blood pressure monitoring techniques suffer from the problems of either being invasive or occluding the flow of blood. Invasive measurement, by way of arterial catheterization has been commonly used in intensive care units and operating rooms for a number of years. However, the risks of infection, thrombus formation, hemorrhage, etc., have given rise to a search for non-invasive approaches which would provide the desired continuous and accurate measurement.

The typical non-invasive approaches taken to date include devices using the so-called tracking cuff principle, e.g., see U.S. Pat. No. 4,524,777. The device disclosed in this patent utilizes a hydraulic servocontrol system to maintain a finger arterial volume constant (in an unloaded state) so that the counter cuff pressure follows the intraarterial blood pressure thus giving an instantaneous arterial blood pressure measurement from the counter cuff pressure. Although this method does provide continuous and non-invasive measurement of arterial blood pressure, long-term maintenance of cuff pressure restrains microcirculation in the finger capillaries and this causes pain. Also, a downward drift occurs for some period of time before stability is reached.

One other non-invasive approach, but which is not continuous, uses a sphygmomanometric technique based on Riva-Rocci's principle in which auscultatory (sound) measurements of blood flow are made to determine the arterial blood pressure (systolic and diastolic only), again using cuff pressure. These measurements are less desirable not only because they are not continuous but also because they are not as accurate.

Another non-invasive approach, known as the oscillometric method, utilizes volume measurements, rather than auscultatory measurements, and cuff pressure to more accurately determine systolic blood pressure. This method also measures mean blood pressure, but not diastolic pressure.

An accurate, non-invasive, continuous and non-occlusive (does not occlude the flow of blood) apparatus and method would be valuable for use in intensive care units and operating rooms to avoid complications which can arise with the above-described prior art devices and methods.

SUMMARY OF THE INVENTION

It is an object of the invention to provide a method and apparatus for measuring arterial blood pressure in a continuous, non-occlusive fashion.

The above and other objects of the invention are realized in a specific illustrative embodiment thereof which includes a continuous, indirect and non-occlusive blood pressure monitor operable under control of a microprocessor. The monitor icludes an annular-inflatable cuff for placement about a patient's finger. Positioned in the cuff are a pressure transducer for producing a signal indicating the cuff pressure, a light emitting diode positioned on one interior side of the cuff, and a photoelectric transducer positioned on the opposite interior side of the cuff. The light emitting diode produces light which is partially transmitted through a patient's finger to the photoelectric transducer which detects the light level or intensity and produces a signal indicating arterial volumetric changes in the finger. The volume-indicating and pressure-indicating signals are amplified and then supplied to anolog-to-digital converters, with the resultant digital output being supplied to the microprocessor. The microprocessor controls a ramp pressure generator which is coupled to the cuff to alternately inflate the cuff (causing the pressure to increase linearly) and deflate the cuff.

The above-described monitor is first used in a calibration cycle in a temporarily occlusive manner to determine certain parameters which will then be used by the monitor to continuously and non-occlusively measure the arterial pressure waveform which includes the mean arterial blood pressure $P_m$, systolic blood pressure $P_s$ and diastolic blood pressure $P_d$, which are the measurements of interest. At first, the microprocessor determines the mean blood pressure $P_m$ and systolic blood pressure $P_s$ in a conventional way (using the well-known oscillometric method) from the measured volume and pressure signals. With the relative volume signal collected during cuff pressure application, the cuff pressure is then relieved. The microprocessor then makes a first estimate of diastolic blood pressure $P_d$ (using a formula for estimating $P_d$ from $P_m$ and $P_s$), and uses that estimated value, along with the measured mean blood pressure and systolic blood pressure, in a recursive procedure based on a pressure-volume relationship known as the Hardy model, to derive a calculated mean blood pressure designated as $P_M$. The calculated mean blood pressure $P_M$ is compared with the measured mean blood pressure $P_m$ and if the difference between the two is greater than some predetermined standard, then a new estimated diastolic blood pressure $P_d$ is used in the recursive procedure to obtain a new mean calculated blood pressure $P_M$. This recursive procedure continues until the calculated mean blood pressure $P_M$ is within a certain range of the measured mean blood pressure $P_m$.

In the course of determining the calculated mean blood pressure $P_M$, three parameters are also developed to define a Hardy model compliance curve for the particular patient in question. These parameters include k which represents the compliance index for the blood vessels of the patient being rreated and is unique to that patient, $V_m$ which represents the maximum volume of the vessels in the patient's finger (being examined), and $V_0$ which represents the volume of the patient's finger vessels at zero pressure. With these parameters determined for the patient, the Hardy model compliance curve may then be used to relate the relative blood vessel volume the patient's arterial blood pressure and vice versa. With the Hardy model parameters and compliance curve for the patient in question being determined, the blood pressure monitor may now be utilized to continuously measure the relative volume $\overline{V}$ as a function of time from which the continuous arterial pressure waveform as a function of time can be determined using the Hardy model.

Periodically, recalibration will be carried out, i.e., new Hardy model parameters will be developed for use in making the continuous blood pressure measurements.

As can be seen, except for the calibration cycle, continous and non-occlusive blood pressure measurement may be carried out. This avoids the pain and trauma of both the invasive blood pressure measuring techniques and the occluding blood pressure measuring techniques.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

The present invention, except for occasional calibration requirements, provides for continuous, noncontactive or nonpressure imposed arterial blood pressure monitoring. The blood pressure measurements, in the form of a pressure waveform, are obtained by calculation from a measured arterial volume signal. The arterial volume signal, which is a relative measurement of the arterial volume over time, is developed using optical sensing techniques which are generally known. The ultimate determination of the pressure waveform is made using the so-called compliance model of Hardy and Collins (hereinafter referred to as the Hardy model) discussed in Hardy, H. H. and Collins, R. E., "On the Pressure-Volume Relationship in Circulatory Elements", Med. and Biol., Eng. and Comput., September, 1982, pages 565–570.

The Hardy model shows that under static conditions, the pressure-volume (P-V) relationship of blood vessels may be described by $$k(V_m - V) = dV/dP, \quad P \geq 0 \tag{1}$$

where P represents the transmural pressure (the difference in pressure inside and outside the artery), $V_m$ is the limiting or maximum volume of the blood vessel in question and k is a physiological constant which characterizes the elasticity of the vascular wall. The constant k is sometimes referred to as the vascular compliance index. Solving the differential equation (1) yields the following pressure/volume relationship $$V = V_m - (V_m - V_0)e^{-kP}, \quad P \geq 0 \tag{2}$$

where $V_0$ is the vessel volume under zero transmural pressure. Equation 2 is referred to as the transformation of the P-V relationship. Combining equations 1 and 2 gives the following equation $$dV/dP = k(V_m - V_0)e^{-kP}, \quad P \geq 0 \tag{3}$$

which defines the vascular compliance of a vessel (unique to each individual).

Figure 2A:
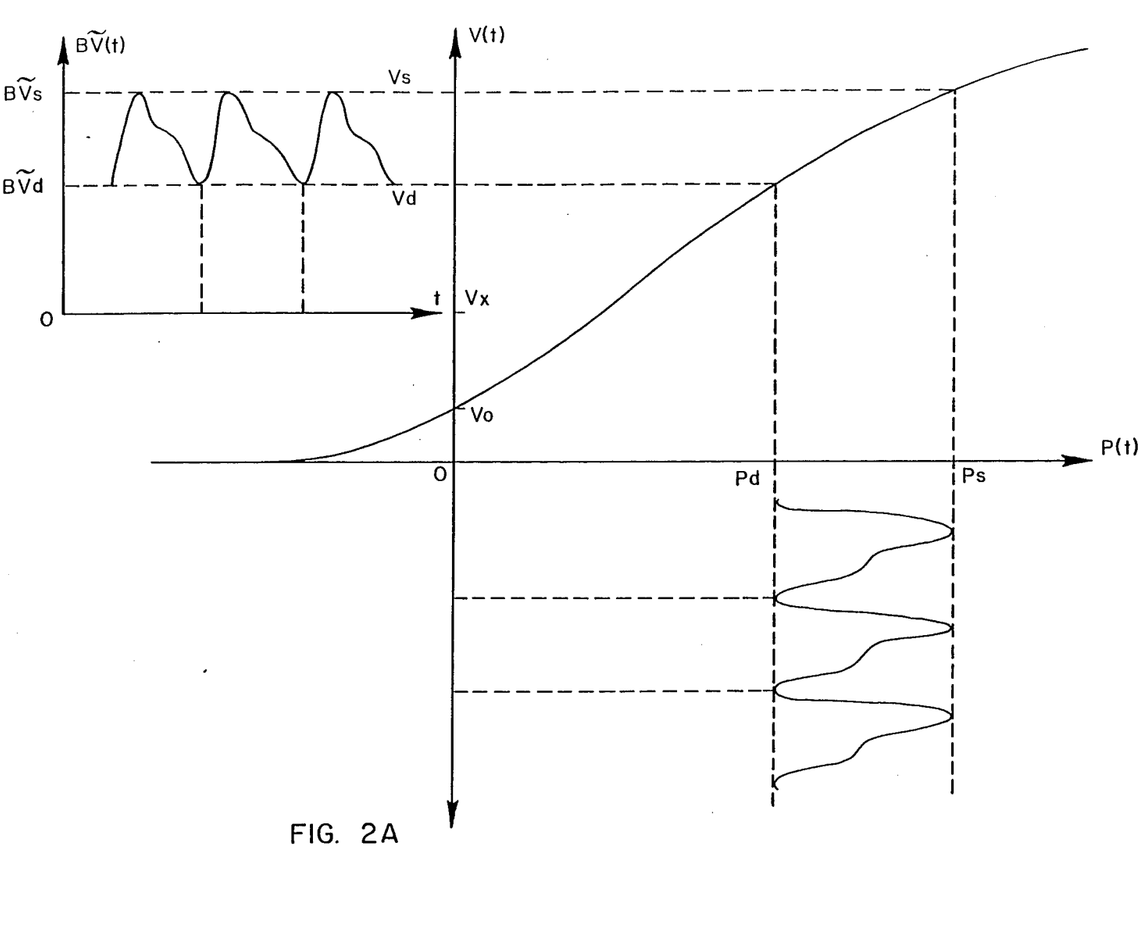
FIGS. 2A through 2C show typical waveforms of the pressure-volume relationship of a blood vessel, of a photoelectric plethysmograph, and of arterial blood pressure, respectively.

With the above described Hardy model, the relationship between pressure P and absolute volume V is established. However, it would be advantageous to define the pressure waveform P(t) in terms of relative volume $\widetilde{V}(t)$ which is a parameter measureable by a photoelectric plethysmogram. The relationship between absolute volume V(t) and relative volume $\widetilde{V}(t)$ is given by $$V(t) = V_x + B\,\widetilde{V}(t) \tag{4}$$

where B is the mapping coefficient from the analog signal $\widetilde{V}(t)$ to the absolute arterial volume as illustrated in FIG. 2A, and $V_x$ is a parameter defining the contribution of tissue absorption of transmitted light emitted by the photoelectric plethysmogram. In other words, there is a linear relationship between the relative volume $\widetilde{V}(t)$ and absolute volume V(t), in which $V_x$ is the intercept, and B is the slope.

Now define systolic volume $V_s$ and diastolic volume $V_d$ in accordance with equations 2 and 4 to get $$V_s = V_m - (V_m - V_0)\,e^{-kP_s} = V_x + B\,\widetilde{V}_s \tag{5}$$

$$V_d = V_m - (V_m - V_0)\,e^{-kP_d} = V_x + B\,\widetilde{V}_d \tag{6}$$

where $\widetilde{V}_s$ and $\widetilde{V}_d$ are analogue systolic and diastolic volumes respectively. Substracting equation 6 from equation 5 gives the mapping coefficient $$B = (V_m - V_0)(e^{-kP_d} - e^{-kP_s})/(\widetilde{V}_s - \widetilde{V}_d) \tag{7}$$

The addition of equation 6 and equation 5 gives the mapping intercept $V_x$.

$$V_x = V_m - (V_m - V_0)(e^{-kP_s} + e^{-kP_d})/2 - \tag{8}$$
$$(\widetilde{V}_s + \widetilde{V}_d)(V_m - V_0)(e^{-kP_d} - e^{-kP_s})/[2(\widetilde{V}_s - \widetilde{V}_d)]$$

Taking the log of both sides of equation 2, substituting equation 4, and rearranging terms, gives the pressure waveform $$\begin{aligned} P(t) &= -1/k \ln\left[(V_m - V(t))/(V_m - V_0)\right] \\ &= -1/k \ln\left[(V_m - (V_x + B\widetilde{V}(t)))/(V_m - V_0)\right] \end{aligned} \tag{9}$$

which may be called the inverse transformation of the P-V relationship with respect to equation 2. Combining equations 7, 8, and 9, the calibrated blood pressure as a function of the analogue arterial volume signal is obtained, i.e., the inverse transformation of P(t)−V(t) relationship, given as $$P(t) = -1/k \ln\;[(e^{-kP_s} + e^{-kP_d})/2 + \tag{10}$$
$$(e^{-kP_d} - e^{-kP_s})((\widetilde{V}_s + \widetilde{V}_d)/2 - \widetilde{V}(t))/(\widetilde{V}_s - \widetilde{V}_d)]$$

where $\widetilde{V}(t)$ is the continuous relative volume as a function of time, $P_s$ is the systolic pressure, $P_d$ is the diastolic pressure, $\widetilde{V}_s$ the systolic relative volume, and $\widetilde{V}_d$ is the diastolic relative volume all of which can be noninvasively measured as will be discussed hereafter. Thus, if these last mentioned parameters and the arterial compliance index k are noninvasively determined in advance, the arterial blood pressure (P(t) when cuff pressure is zero) can be developed by measuring the relative volume $\widetilde{V}(t)$ and using equation (10).

The relative systolic volume $\widetilde{V}_s$ and relative diastolic volume $\widetilde{V}_d$ may be non-invasively determined in a conventional fashion as shown in FIG. 2A. The systolic pressure $P_s$ may be non-invasively determined using conventional oscillometric methods, as mentioned earlier. Specifically, the systolic pressure may be determined by the cuff pressure at which the pulsatile plethysmograph developed using the oscillometric method disappears. This is well known in the art. The diastolic pressure $P_d$ cannot be determined directly from pulsatile information of a plethysmograph, but can be determined using an iterative procedure to be descibed momentarily. Calculation of the compliance index k is dependent on parameters which include the diastolic pressure $P_d$. The iterative procedure to be described will yield both $P_d$ and k to thus provide the five parameters $\widetilde{V}_s$, $\widetilde{V}_d$, $P_s$, $P_d$ and k needed in equation 10.

Figure 2B:
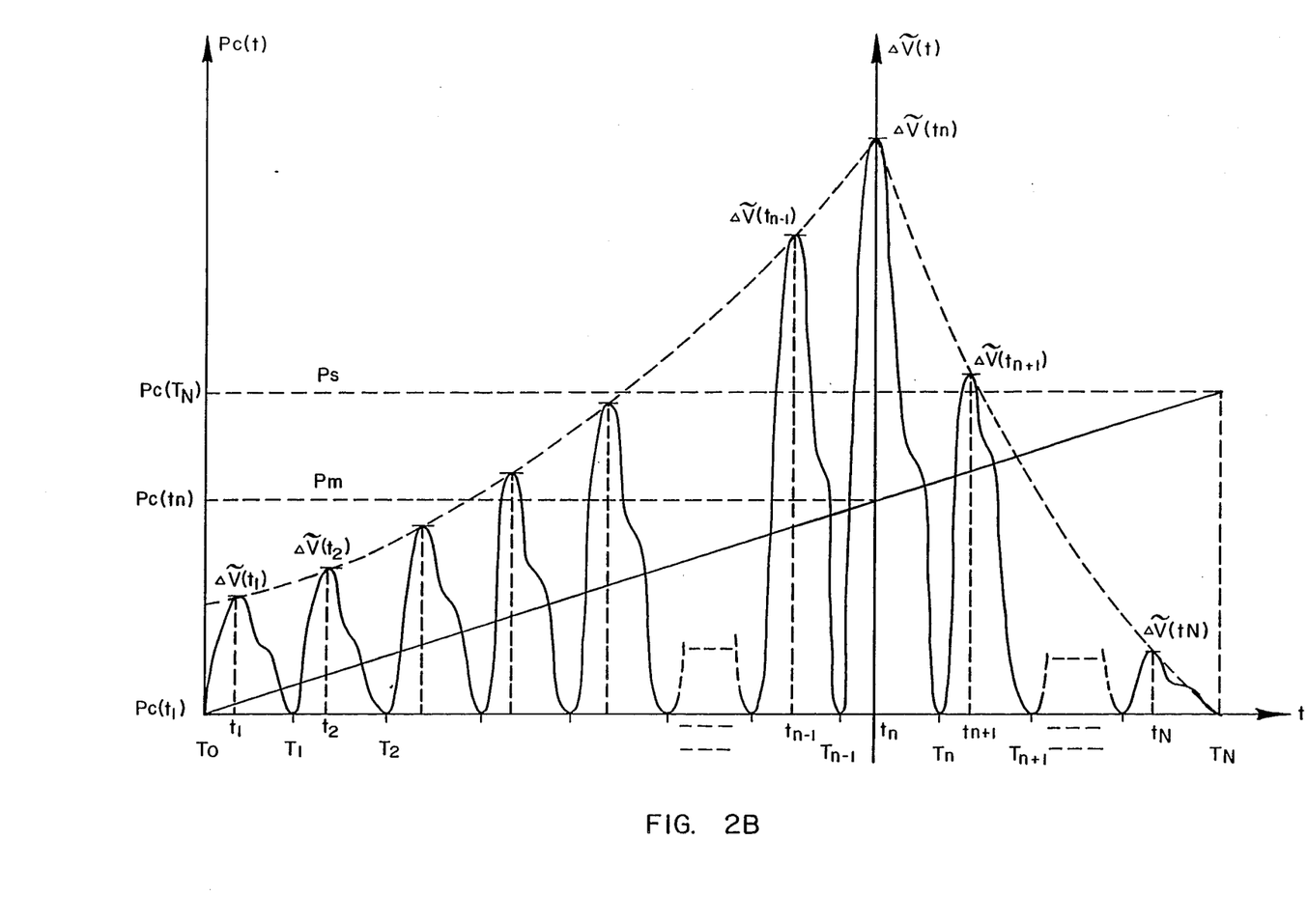
Figure 2C:
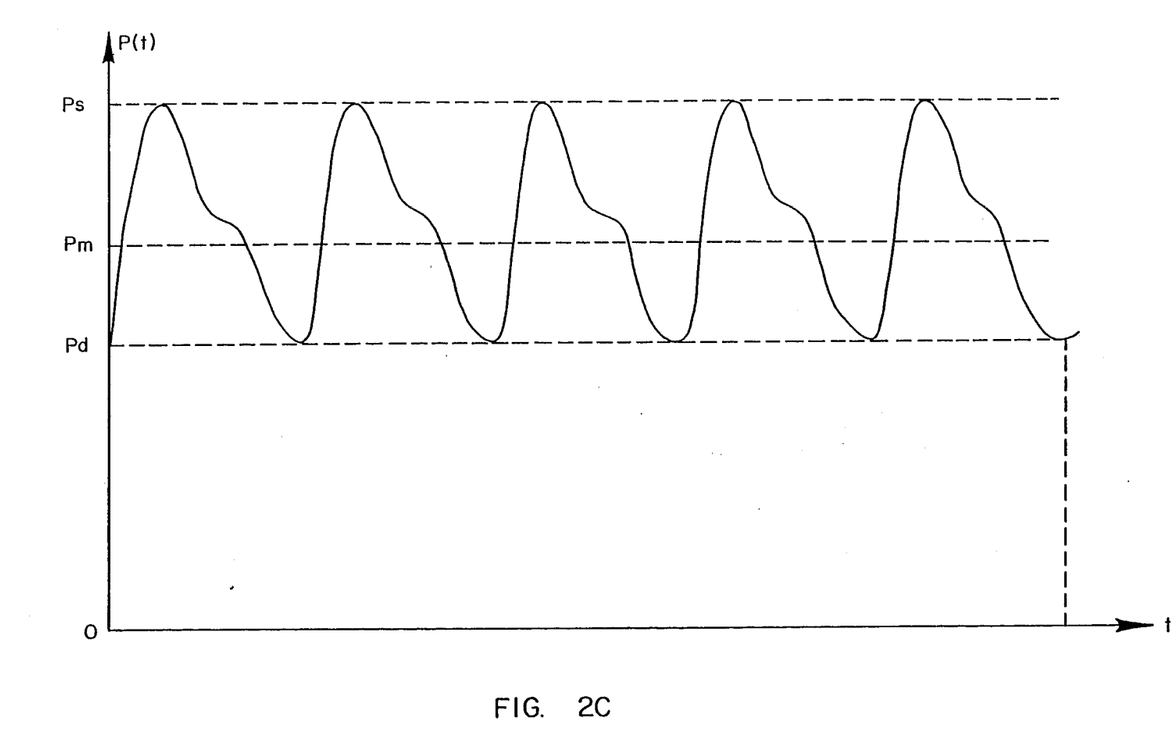

A least square approach may be used to determine the compliance index k which will now be described. First, refer to FIG. 2B which shows the photoelectric plethysmograph volume $\Delta \widetilde{V}$ under the corresponding transmural pressure $P = P_b - P_c$, where $P_b$ and $P_c$ are intra-arterial and cuff (measured) pressures respectively. Note the established fact that the amplitude of the pulsatile volume $\Delta \widetilde{V}$ is maximum when $P_c$ equals the mean blood pressure $P_m$ (see FIG. 2B). Equation 3 can be used to relate mean blood pressure $P_m$ cuff pressure $P_c$, the amplitude of pulsatile photoelectric plethysmograph $\Delta \widetilde{V}$, and pulsatile blood pressure $\Delta P$ as follows:

$$\Delta \widetilde{V}/\Delta P \approx k(\widetilde{V}_m - \widetilde{V}_0)e^{-k(P_m - P_c)}, \quad (11)$$

where $\Delta P = (P_s - P_c) - (P_d - P_c) = P_s - P_d$, $P_s$ and $P_d$ being systolic and diastolic blood pressure respectively. Assume that intra-arterial blood pressure remains the same in the time of calibration, i.e., ramp cuff pressure application. A set of n equations representing the same relationship of equation 11, under different ramp cuff pressures can then be acquired as follows $$\Delta \widetilde{V}_1/\Delta P = k(\widetilde{V}_m - \widetilde{V}_0) e^{-k(P_m - P_{c1})} \quad (12)$$

$$\Delta \widetilde{V}_2/\Delta P = k(\widetilde{V}_m - \widetilde{V}_0) e^{-k(P_m - P_{c2})}$$

...

$$\Delta \widetilde{V}_n/\Delta P = k(\widetilde{V}_m - \widetilde{V}_0) e^{-k(P_m - P_{cn})}$$

Equation set 12 is linearized by taking the natural logarithm with respect to equation 11, giving $$\ln(\Delta \widetilde{V}/\Delta P) = kP_c + [\ln[k(\widetilde{V}_m - \widetilde{V}_0)] - kP_m] \quad (13)$$

which has the linear form of $$y = ax + b \quad (14)$$

where $$x = P_c, y = \ln(\Delta \widetilde{V}/\Delta P) \quad (15)$$
$$a = k, b = \ln[k(\widetilde{V}_m - \widetilde{V}_0)] - kP_m$$

which transforms the set of n nonlinear equations 12 into the set of n linear equations, given as $$y_1 = ax_1 + b \quad (16)$$
$$y_2 = ax_2 + b$$

...

$$y_n = ax_n + b$$

where $y_i = \ln(\Delta \widetilde{V}_i/\Delta P), x_i = P_{ci}, (i=1,2,\ldots,n)$ The coefficients and their uncertainties are obtained from equation set 16 applying standard least mean square error analysis, thus providing the estimate of the arterial compliance index k of the Hardy model, in terms of x and y, i.e., $$k = \frac{\left[\sum_{i=1}^{n} e^{2y_i} x_i y_i - \left(\sum_{i=1}^{n} e^{2y_i}\right) XY\right]}{\left[\sum_{i=1}^{n} e^{2y_i} x_i^2 - \left(\sum_{i=1}^{n} e^{2y_i}\right) X^2\right]} \quad (17)$$

in which $$X = \left[\sum_{i=1}^{n} e^{2y_i} x_i\right] / \left[\sum_{i=1}^{n} e^{2y_i}\right], \quad (18)$$

$$Y = \left[\sum_{i=1}^{n} e^{2y_i} y_i\right] / \left[\sum_{i=1}^{n} e^{2y_i}\right].$$

Had an accurate estimate of $P_d$ been used in equations 15–17, the Hardy model parameters would be correctly determined. However, to obtain an accurate value for $P_d$, the following iterative procedure is used:

1. Select an initial value of $P_d$ to be $P_{dj} = 3/2\ P_m - \frac{1}{2} P_s$ where $P_m$ and $P_s$ are measured using known oscillometric methods.

2. Calculate the compliance index $k_j$ based on $P_{dj}$ using equation 17.

3. Calculate $P(t)_j$ in accordance with equation 10 using $k_j$ and the measured relative volume $\widetilde{V}(t)$.

4. Calculate a mean pressure in accordance with the formula $$P_{Mj} = 1/T \int_o^T P(t)_j \, dt \quad (19)$$

5. Compare the calculated mean pressure $P_{Mj}$ with the measured mean presure $P_m$ and if the difference is less than one mmHg the procedure is stopped, otherwise another "estimated" diastolic pressure $P_{d(j+1)}$ is determined by the gradient method from the formula $$P_{d(j+1)} = P_{dj} - (P_m - P_{mj}) \partial(P_m - P_{mj})/\partial P_{dj} \quad (20)$$

The procedure then returns to step 2 above.

When the procedure yields a calculated mean pressure which is within the predetermined range of the measured mean pressure, needed parameters for the Hardy model will have been obtained, namely k, $V_m$ and $V_0$. In effect, the parameters necessary to develop a Hardy model compliance curve for a patient are determined by the above iterative procedure. With this information, the blood pressure waveform P(t) can be produced from the measured relative volume $\widetilde{V}(t)$ on a continuous, nonocclusive basis.

Figure 1:
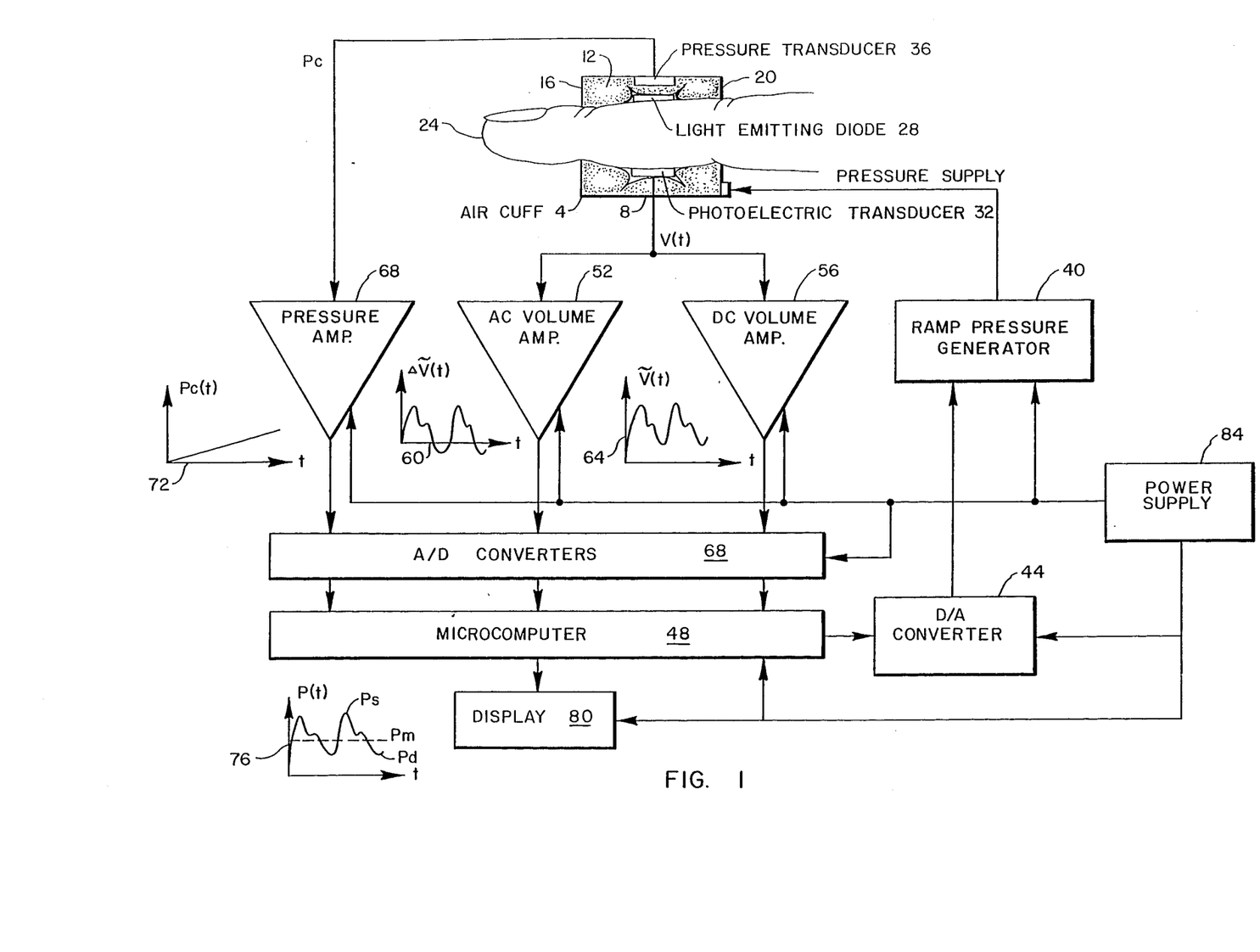
FIG. 1 is a circuit diagram of an automatic, continuous and non-occlusive blood pressure monitor made in accordance with the principles of the present invention.

Apparatus for carrying out the desired measurements, both for obtaining the parameters for the Hardy model and for producing the waveform P(t), is shown in FIG. 1. The apparatus includes an inflatable annular finger cuff 4 having a rigid outer wall 8 and a resilient inflatable annular bag 12 held in place by inwardly extending end walls 16 and 20. The bag 12 is filled with air or other fluid for producing a pressure on a finger 24 when the finger is inserted into the cuff. Disposed on the interior wall of the bag 12 between the bag and the finger 24 and on one side of the cuff 4 is a light emitting diode 28. Disposed on the interior wall of the bag 12 on the other side of the cuff 4 is a photoelectric transducer 32 for detecting light transmitted from the light emitting diode 28 through the finger 24 to the photoelectric transducer. The amount of light reaching the transducer 32 is proportional to the volume of the blood vessel or vessels positioned between the diode 28 and transducer 32. The output signal of the transducer therefore represents the relative volum $\widetilde{V}(t)$ of the blood vessel or vessels in question.

Disposed inside the bag 12 is a pressure transducer 36 for producing a signal representing the cuff pressure $P_c$ being applied to the finger 24 by the bag 12 when it is inflated. A ramp pressure generator 40, of conventional design, supplies air to the cuff 4 in response to analog signals from a digital-to-analog converter 44 which receives the digital counterparts of the analog signals form a microprocessor or microcomputer 48. The microcomputer produces signals for causing the ramp pressure generator 40 to alternately inflate the bag 12 with a linearly increasing ramp pressure, and then deflate the bag.

The relative volume signal $\widetilde{V}(t)$ produced by the photoelectric transducer 32 is supplied to an A.C. volume amplifier 52 which amplifies the A.C. component of the relative volume signal, and to a D.C. volume amplifier 56 which amplifies the total relative volume signal. The outputs of the two amplifiers 52 and 56 shown graphically at 60 and 64 respectively are supplied to analog-to-digital converters 68 where the analog signals are converted to digital form for application to the microcomputer 48. The output $P_c$ of the pressure transducer 36 is also supplied to an amplifier 68 which amplifies the signal shown at 72 for application to the analog-to-digital converters 68 for conversion to digital form and ultimate transfer to the microcomputer 48.

The signals received from the analog-to-digital converters 68 are used by the microcomputer to both calculate the parameters needed for the Hardy model (calibration for a particular patient), and produce the arterial blood pressure waveform P(t), shown at 76, from which the systolic, diastolic and mean blood pressures can be obtained. This information is displayed in real time on a display unit 80 which might illustratively include a CRT and digital displays. A power supply unit 84 provides power for operation of the monitor.

Use of the blood pressure monitor shown in FIG. 1 will now be described. A patient whose blood pressure is to be determined inserts his finger into the annular cuff 4, and the bag 12 is inflated to apply pressure to the finger. As this is being done, relative volume signals $\widetilde{V}(t)$ and cuff pressure signals $P_c$ are developed by the photoelectric transducer 32 and pressure transducer 36 respectively and supplied to corresponding amplifiers. The signals are amplified and supplied to the analog-to-digital converters 68, with the digital versions being supplied to the microcomputer 48. From these signals, the microcomputer 48 develops the mean pressure $P_m$ and systolic pressure $P_s$ using conventional oscillometric methods. The cuff pressure is then released so that there is no occlusion of the finger blood vessels. The microcomputer 48 then begins the iterative procedure described earlier by calculating a first estimated diastolic pressure $P_d$ which, along with the measured mean pressure and systolic pressure are used to obtain Hardy model parameters for defining a Hardy model compliance curve. From this compliance curve, a blood pressure waveform P(t) is generated and then from that a mean pressure $P_M$ is calculated. The calculated mean pressure $P_M$ is then compared with the measured mean pressure $P_m$ and if the two are not within a certain range of each other, another estimate for diastolic pressure $P_d$ is made and the procedure for calculating a mean pressure is repeated. When the calculated mean pressure is within the desired range of the measured mean pressure, the iterative procedure is stopped and the Hardy model parameters which had led to the last calculated mean pressure are stored since they define a Hardy model compliance curve which will be used to continuously monitor blood pressure. Thereafter, the photoelectric transducer 32 produces a relative volume signal $\widetilde{V}(t)$ from which the microcomputer 48 calculates the arterial pressure waveform P(t) as desired.

Recalculation of the Hardy model compliance curve for the patient in question may be carried out periodically since it has been found that the parameters tend to change over time.

In the manner described, continuous and noncontactive arterial blood pressure measurements may be made with the blood pressure monitor of FIG. 1.

It is to be understood that the above-described arrangements are only illustrative of the aplication of the principles of the present invention. Numerous modifications and alternative arrangements may be devised by those skilled in the art without departing from the spirit and scope of the present invention and the appended claims are intended to cover such modifications and arrangements. For example, sensing light reflected from rather than transmitted through an artery could be utilized to determine relative volume of the artery.

What is claimed is:

1. An apparatus for automatically measuring a person's blood pressure comprising:
    means for applying pressure to a body part of the person in response to a pressure supply signal, and for temporarily occluding the flow of blood on said body part by application of said pressure;
    means for directing light toward the body part and an artery in the body part;
    means for directing the intensity of light passing through or reflected by the body part and artery and for producing therefrom a signal $\widetilde{V}(t)$ representing the relative volume of a unit length of the artery, and having an AC component and DC component;
    means for detecting the pressure applied to the body part and producing a signal $P_c(t)$ representing said detected pressure; and
    processor means for
    (a) calculating means pressure $P_m$ and systolic pressure $P_s$ from said signal $P_c(t)$ and said AC component of said signal $\widetilde{V}(t)$
    (b) thereafter controlling said means for applying pressure so as to remove the pressure from the body part,
    (c) calculating a formulation of arterial pressure P(t) as a function of relative arterial volume $\widetilde{V}(t)$ using said means pressure $P_m$ and systolic pressure $P_s$, and
    (d) for continuously using said signal $\widetilde{V}(t)$ for calculating the arterial pressure P(t) of the person from said signal $\widetilde{V}(t)$.

2. Apparatus as in claim 1 further comprising display means coupled to the processor means for displaying the calculated arterial pressure P(t).

3. Apparatus as in claim 1 wherein said processor means comprises a microprocessor.

4. A process for automatically measuring the blood pressure of a person comprising the steps of
   (a) temporarily occluding the flow of blood on a body part of the person by application of a pressure,
   (b) directing light toward the body part and an artery in the body part,
   (c) detecting the intensity of light passed through or reflected by the body part and artery and producing therefrom a signal $P_c(t)$ representing the relative volume of a unit length of the artery, and having an AC component and DC component,
   (d) detecting the pressure applied to the body part and producing a signal $P_c(t)$ representing that pressure,
   (e) calculating mean pressure $P_m$ and systolic pressure $P_s$ from the signal $P_c(t)$ and AC component of the signal $\widetilde{V}(t)$,
   (f) removing the pressure from the body part,
   (g) calculating a formulation of arterial pressure $P(t)$ as a function of a relative arterial volume $\widetilde{V}(t)$ using the mean pressure $P_m$ and systolic $P_s$,
   (h) continuously produce the signal $\widetilde{V}(t)$ as in step (c) but without application of pressure to said part, and
   (i) calculating the arterial pressure $P(t)$ of the person from the signal $\widetilde{V}(t)$. person from signal $\widetilde{V}(t)$.

5. A process as in claim 4 wherein steps (a) and (f) comprise automatically applying pressure to and removing pressure from the body part under control of a microprocessor.

6. A process as in claim 4 wherein step (g) comprises the steps of
   (j) calculating parameters for the Hardy model compliance curve for the person, represented by $$k(V_m - V) = dV/dP, \ P \geq 0$$

where k is the compliance index of the vascular wall of the artery and $V_m$ is the maximum volume of the artery, and
   (k) transforming the equation of step (j) to define arterial pressure $P(t)$ as a function of relative arterial volume $\widetilde{V}(t)$.

7. A process as in claim 4 wherein step (g) comprises
   (l) selecting a value for diastolic pressure $P_d$ to be $$P_{dj} = 3/2 \ P_m - \tfrac{1}{2} \ P_s,$$

(m) calculating the compliance index $k_j$ from the following $$k = \frac{\left[\sum_{i=1}^{n} e^{2y_i} x_i y_i - \left(\sum_{i=1}^{n} e^{2y_i}\right) XY\right]}{\left[\sum_{i=1}^{n} e^{2y_i} x_i^2 - \left(\sum_{i=1}^{n} e^{2y_i}\right) X^2\right]}$$

where $$X = \left[\sum_{i=1}^{n} e^{2y_i} x_i\right] / \left[\sum_{i=1}^{n} e^{2y_i}\right],$$

$$Y = \left[\sum_{i=1}^{n} e^{2y_i} y_i\right] / \left[\sum_{i=1}^{n} e^{2y_i}\right].$$

$x_i = P_{ci}$, and $y_i = \ln(\Delta V_i / \Delta P),$ (n) calculating arterial pressure $P(t)_j$ from the following $$P(t)_j = -1/k_j \ln \ [(e^{-kP_s} + e^{-kP_{dj}})/2 + (e^{-kP_{dj}} - e^{-kP_s})((\widetilde{V}_s + \widetilde{V}_d)/2 - \widetilde{V}(t))/(\widetilde{V}_s - \widetilde{V}_d)]$$

where $\widetilde{V}(t)$ represents relative arterial volume,
   (o) calculating a mean pressure $P_{Mj}$ from the following $$P_{Mj} = 1/T \int_0^T P(t)_j \, dt,$$

(p) Selecting another value of diastolic pressure to be $$P_{d(j+1)} = P_{dj} - (P_m - P_{Mj}) \partial (P_m - P_{Mj}) / \partial P_{dj}$$

repeating steps (m) through (p) if the difference between $P_{Mj}$ and $P_m$ is greater than a predetermined value, and
   (q) using the most recently calculated value of $K_j$ in the process of measuring arterial blood pressure if the difference between $P_{Mj}$ and $P_m$ is less than the predetermined value.

* * * * *

UNITED STATES PATENT AND TRADEMARK OFFICE
CERTIFICATE OF CORRECTION

PATENT NO. : 4,846,189

DATED : July 11, 1989

INVENTOR(S) : Shuxing Sun

It is certified that error appears in the above-identified patent and that said Letters Patent is hereby corrected as shown below:

Column 1, line 10, "nonn-contactive" should be --non-contactive--
Column 1, line 65, "icludes" should be --includes--
Column 2, line 58, "volume the" should be --volume V to--
Column 3, line 68, "measureable" should be --measurable--
Column 10, line 29, "$e^{-kP}s)$" should be --$e^{-k_j P_s}$--

Signed and Sealed this

Seventeenth Day of March, 1992

Attest:

HARRY F. MANBECK, JR.

Attesting Officer

Commissioner of Patents and Trademarks